(12) United States Patent
Groenland et al.

(10) Patent No.: US 11,583,193 B2
(45) Date of Patent: Feb. 21, 2023

(54) WIRELESS INTRALUMINAL DEVICE AND SYSTEM

(71) Applicant: KONINKLIJKE PHILIPS N.V., Eindhoven (NL)

(72) Inventors: Alfons Wouter Groenland, Best (NL); Arjen Van Der Horst, Tilburg (NL); Derk Reefman, Best (NL); David Holt Burkett, Panama City Beach, FL (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 375 days.

(21) Appl. No.: 16/348,919

(22) PCT Filed: Nov. 9, 2017

(86) PCT No.: PCT/IB2017/056997
§ 371 (c)(1),
(2) Date: May 10, 2019

(87) PCT Pub. No.: WO2018/087683
PCT Pub. Date: May 17, 2018

(65) Prior Publication Data
US 2019/0269335 A1    Sep. 5, 2019

Related U.S. Application Data

(60) Provisional application No. 62/421,882, filed on Nov. 14, 2016.

(51) Int. Cl.
*A61B 5/0215*    (2006.01)
*A61B 5/00*    (2006.01)
(Continued)

(52) U.S. Cl.
CPC .......... *A61B 5/0215* (2013.01); *A61B 5/0002* (2013.01); *A61B 5/002* (2013.01);
(Continued)

(58) Field of Classification Search
CPC ..... A61B 5/0215; A61B 5/0002; A61B 5/026; A61B 5/6851; A61B 5/6852; A61B 2562/0247; A61B 2562/227
See application file for complete search history.

(56) References Cited

U.S. PATENT DOCUMENTS 4,632,121 A * 12/1986 Johnson ................. H01R 13/20
600/372
2007/0179552 A1    8/2007 Dennis et al.
(Continued)

FOREIGN PATENT DOCUMENTS

JP    9164215 A    6/1997
WO    2015085220 A1    6/2015

OTHER PUBLICATIONS

International Search Report and Written Opinion, International Application No. PCT/IB2017/056997, dated Feb. 2, 2018.

*Primary Examiner* — Daniel L Cerioni

(57) ABSTRACT

A wireless intraluminal device (102) and an associated system for treating and diagnosing patients are provided. In one embodiment, the wireless intraluminal device (102) includes a flexible elongate member (158) including a proximal portion (106) and a distal portion (108); a sensor assembly (116) coupled to the distal portion of the flexible elongate member; a cable (117) coupled to the sensor assembly and extending along the flexible elongate member; and a wireless transceiver (252) positioned within the flexible elongate member, wherein the wireless transceiver is in communication with the sensor assembly via the cable. A wireless communication component (104) wirelessly transmits a sensor measurement collected by the sensor assembly (Continued)

to a sensor measurement processing system (132) via a wireless link (150) for physiological data generation at the sensor measurement processing system.

8 Claims, 8 Drawing Sheets

(51) Int. Cl.
*A61B 5/026* (2006.01)
*A61B 5/0295* (2006.01)
*A61B 5/0285* (2006.01)

(52) U.S. Cl.
CPC ............ *A61B 5/026* (2013.01); *A61B 5/0285* (2013.01); *A61B 5/0295* (2013.01); *A61B 5/686* (2013.01); *A61B 5/6851* (2013.01); *A61B 5/6852* (2013.01); *A61B 2505/03* (2013.01); *A61B 2505/05* (2013.01); *A61B 2562/0247* (2013.01); *A61B 2562/164* (2013.01); *A61B 2562/227* (2013.01); *A61M 2205/3523* (2013.01)

(56) References Cited

U.S. PATENT DOCUMENTS

| | | | |
|---|---|---|---|
| 2008/0188890 A1* | 8/2008 | Weitzner | A61B 1/00165 606/205 |
| 2009/0124880 A1 | 5/2009 | Smith | |
| 2011/0117974 A1* | 5/2011 | Spitalnik | H01R 31/06 455/573 |
| 2013/0204111 A1 | 8/2013 | Flanders | |
| 2014/0187874 A1 | 7/2014 | Burkett et al. | |
| 2014/0187981 A1 | 7/2014 | Millett et al. | |
| 2015/0150505 A1* | 6/2015 | Kaskoun | A61B 5/7405 600/300 |
| 2016/0058977 A1 | 3/2016 | Burkett et al. | |
| 2017/0049359 A1* | 2/2017 | Arevalos | A61B 5/02042 |

* cited by examiner

WIRELESS INTRALUMINAL DEVICE AND SYSTEM

CROSS-REFERENCE TO PRIOR APPLICATIONS

This application is the U.S. National Phase application under 35 U.S.C. § 371 of International Application No. PCT/IB2017/056997, filed on 9 Nov. 2017, which claims the benefit of U.S. Provisional Patent Application No. 62/421,882, filed on 14 Nov. 2016. These applications are hereby incorporated by reference herein.

TECHNICAL FIELD

The present disclosure relates generally to intraluminal functional assessment and, in particular, to providing wireless communication between a function measurement (FM) intraluminal device and a sensing measurement processing system for display and control.

BACKGROUND

Assessing the functional significances of cardiovascular and peripheral vascular diseases by intraluminal pressure and/or flow measurements can be beneficial to guide treatments of atherosclerotic diseases. Intraluminal devices with functional measurement (FM) capabilities have been developed to perform various types of measurements. For example, an intraluminal device may include a pressure sensor and/or a flow sensor at the tip of the intraluminal device. The intraluminal device may be inserted into a vessel of a patient body and the pressure sensor and/or the flow sensor may measure pressure and/or flow within the vessel. In particular, indices have been developed for coronary arteries to guide cardiologists in the decision of treating lesions. Examples of pressure-based indices may include fractional flow reserve (FFR) and instantaneous wave free ratio (iFR). An example of flow-based indices may include coronary flow reserve (CFR). An example of a combination of pressure-based and flow-based indices may include hyperemic stenosis resistance (HSR). These pressure-based and/or flow-based indices can provide better guidance to treatment decisions compared to angiographic assessment alone.

The operations of an intraluminal device may require several wire connections, for example, for receiving power and for communication with a console for display and control. For example, the sensors may receive power via the wire connections for performing sensing measurements and the measurements may be output to the console via the wire connections.

Intraluminal procedures may be performed in catheter labs and office-based labs (OBLs). The use of intraluminal devices in catheter labs and OBLs increases the number of cables in the catheter labs and OBLs and may clutter the workspace of the catheter labs and the OBLs. In addition, sterilization is important when operating in a catheter lab or an OBL. The connecting and/or disconnecting of an unsterile console or processing system to a sterile intraluminal device may be an issue in the catheter labs and the OBLs.

SUMMARY

Embodiments of the present disclosure provide a wireless intraluminal device. The wireless intraluminal device includes a flexible elongate member, sensor assembly mounted at a distal portion of the flexible elongate member, and a wireless transceiver configured in various configurations within the flexible elongate member.

In one embodiment, a wireless intraluminal device includes a flexible elongate member including a proximal portion and a distal portion; a sensor assembly coupled to the distal portion of the flexible elongate member; a cable coupled to the sensor assembly and extending along the flexible elongate member; and a wireless transceiver positioned within the flexible elongate member, wherein the wireless transceiver is in communication with the sensor assembly via the cable.

In some embodiments, the wireless intraluminal device further includes an antenna communicatively coupled to the wireless transceiver. In some embodiments, the wireless transceiver is positioned within the proximal portion of the flexible elongate member, and wherein the antenna extends from the wireless transceiver and along an outer surface of the proximal portion of the flexible elongate member. In some embodiments, the wireless transceiver is positioned within a central portion of flexible elongate member between the proximal portion and the distal portion, and wherein the antenna extends along an outer surface of the proximal portion of the flexible elongate member. In some embodiments, the wireless transceiver is positioned within a central portion of flexible elongate member between the proximal portion and the distal portion, and wherein the antenna extends within the proximal portion of the flexible elongate member. In some embodiments, the wireless transceiver is positioned within the distal portion of the flexible elongate member, and wherein the antenna extends along an outer surface of the proximal portion of the flexible elongate member. In some embodiments, the wireless transceiver is positioned within the distal portion of the flexible elongate member, and wherein the antenna extends along within the proximal portion of the flexible elongate member. In some embodiments, the wireless intraluminal device further includes an electrical interface coupled to the proximal portion of the flexible elongate member; and a connector coupled to the proximal portion of the flexible elongate member, wherein the connector includes a power source coupled to the electrical interface, and wherein the power source powers the sensor assembly and the wireless transceiver. In some embodiments, the connector is detachable from the flexible elongate member. In some embodiments, the electrical interface includes a first electrical contact coupled to a positive terminal of the power source; and a second electrical contact coupled to a negative terminal of the power source. In some embodiments, the electrical interface includes a third electrical contact coupled to the antenna. In some embodiments, the wireless intraluminal device further includes a connector coupled to the proximal portion of the flexible elongate member; and an antenna mechanically coupled to the connector. In some embodiments, the sensor assembly includes at least one of a pressure sensor or a flow sensor.

In one embodiment, a wireless intraluminal system for treating a patient includes an intraluminal device including a flexible elongate member having a proximal portion and a distal portion; a sensor assembly coupled to the distal portion of the flexible elongate member; a cable coupled to the sensor assembly and extending along the flexible elongate member; and a first wireless communication component positioned within the flexible elongate member, wherein the first wireless communication component is in communication with the sensor assembly via the cable; a second wireless communication component in communication with the first wireless communication component of the intraluminal device via a wireless link; and a sensor measurement processing component in communication with the second wireless communication component, wherein the first wireless communication component wirelessly transmit, to the second wireless communication component via the wireless link, a sensor measurement collected by the sensor assembly for physiological data generation at the sensor measurement processing component.

In some embodiments, the wireless intraluminal system further includes a display component in communication with the sensor measurement processing component, wherein the sensor measurement processing component generates physiological data based on the sensor measurement, and wherein the display component displays the physiological data. In some embodiments, the second wireless communication component wirelessly transmits, to the first wireless communication component via the wireless link, an instruction to control the sensor assembly for the physiological data generation.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
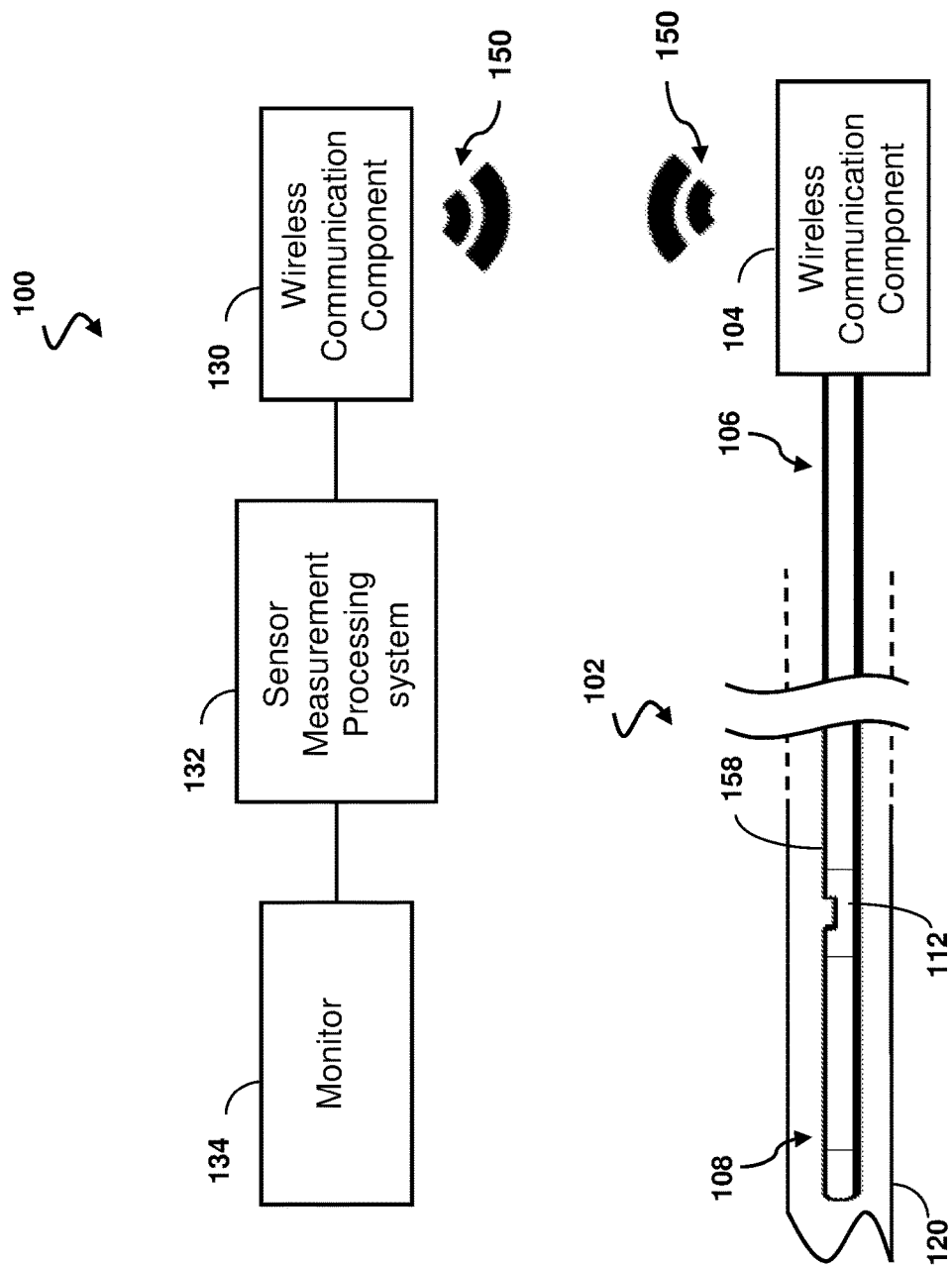
FIG. 1 is a schematic diagram of a wireless functional intraluminal system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Disclosed herein are various embodiments of providing a wireless intraluminal device. The intraluminal device includes sensor assembly, a flexible elongate member, a wireless communication component, and a detachable battery pack. The flexible elongate member includes a proximal portion and a distal portion. The sensor assembly is coupled to the distal portion of the flexible elongate member. The intraluminal device includes a cable coupled to the sensor assembly and extending along a length of the flexible elongate member. The detachable battery pack is coupled to a proximal portion of the flexible elongate member. The wireless communication component can wirelessly receive instructions for controlling the sensor assembly. The wireless communication component can wirelessly transmit sensor measurements collected by the sensor assembly for analysis, interpretation, and physiological data generation at a processing system. The wireless communication component includes a wireless transceiver and an antenna, which may be positioned at various locations within the intraluminal device. Although the disclosed embodiments are described in the context of pressure and/or flow sensing, the disclosed embodiments are suitable for use in any other medical sensing and/or treatment applications.

The disclosed embodiments may provide several benefits over wired intraluminal devices. For example, the use of wireless intraluminal devices reduces the number of cables required in a catheter lab, and thus reduces cluttering of catheter lab workspaces. In a wired intraluminal system, galvanic isolation is important and is typically implemented in a patient isolation module (PIM) connecting to an intraluminal device. The wireless solution provides automatic galvanic isolation and eliminates the need for a PIM.

FIG. 1 is a schematic diagram of a wireless intraluminal system 100, according to aspects of the present disclosure. The system 100 may include a wireless intraluminal device 102, a wireless communication component 130, a sensor measurement processing system 132, such as a console and/or a computer, and a monitor 134. The intraluminal device 102 may include a flexible elongate member 158, which may be a catheter, a guide wire, or a guide catheter, coupled to a wireless communication component 104.

The flexible elongate member 158 includes a distal portion 108, a proximal portion 106, and a housing 112 positioned adjacent to the distal portion 108. The housing 112 may be positioned at a distance (e.g., about 3 centimeters (cm)) from a distal tip of the intraluminal device 102. The housing 112 may include a sensor assembly (shown in FIGS. 3 and 4), which may include one or more sensors, transducers, and/or other monitoring elements configured to obtain diagnostic information about a vessel 120.

The intraluminal device 102 may further include a cable (a cable 117 shown in FIGS. 2 and 4) coupled to the sensor assembly in the housing 112 to provide communication between the sensor assembly and the wireless communication component 104, as described in greater detail herein. Although the wireless communication component 104 is shown to be coupled to the proximal portion 106 of the flexible elongate member 158, the wireless communication component 104 may be configured in various configurations within the intraluminal device 102, as described in greater detail herein.

At a high level, the sensor assembly measures physiological characteristics, which may be pressure and/or flow, of fluid in the vessel 120 and the communication cable transfers the sensor measurements to the wireless communication component 104. The wireless communication component 104 wirelessly transmits sensor output signals carrying the sensor measurements, for example, in a radio frequency (RF) band, as shown by the RF signals 150. Upon receiving the sensor output signals, the wireless communication component 130 transfers the sensor output signals to the sensor measurement processing system 132. The sensor measurement processing system 132 interprets and analyzes the sensor measurements and produces physiological data, graphs, readings and/or diagnostic information for display on the monitor 134. The sensor assembly in the housing 112, the wireless communication component 104, and associated components for signal controls and transfers are described in greater detail herein.

The sensor measurement processing system 132 can include a processor and a memory. The sensor measurement processing system 132 can be operable to facilitate the features of the system 100 described herein. For example, the processor can execute computer readable instructions stored on the non-transitory tangible computer readable medium.

In some embodiments, the wireless communication components 104 and 130 may include substantially similar functional components, but may have different physical form factors and arrangements. The wireless communication components 104 and 130 may operate at a data rate in a range of a few kilobits per second (kbps). Some examples of wireless communication protocols suitable for transferring functional measurements may include Bluetooth, Zigbee, and ultra-wideband (UWB).

Figure 2:
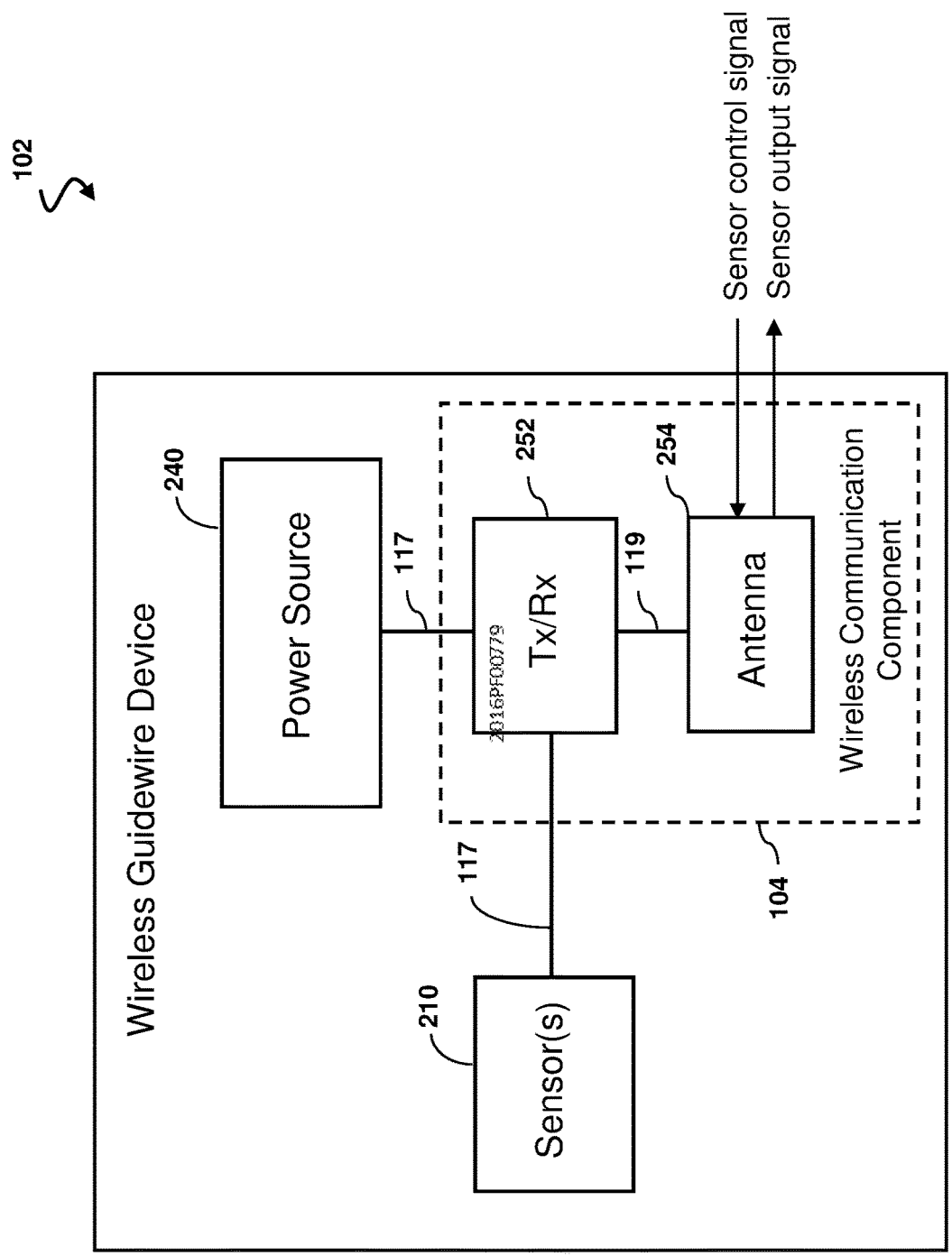
FIG. 2 is a schematic diagram illustrating a wireless intraluminal device architecture, according to aspects of the present disclosure.

FIG. 2 is a schematic diagram illustrating the wireless intraluminal device 102 architecture, according to aspects of the present disclosure. FIG. 2 provides a more detail view of the internal components of the intraluminal device 102. As shown, the intraluminal device 102 includes one or more sensors 210, a power source 240, and the wireless communication component 104. The sensors 210 may include pressure and/or flow sensors and associated electronics (e.g., a low noise amplifier (LNA)). The sensors 210 may be part of the sensor assembly housed in the housing 112. The power source 240 may be a battery pack, super capacitors, or any suitable electrical energy storage that powers the sensors 210 and the wireless communication component 104. The sensors 210, the wireless communication component 104, and the power source may be coupled via a cable 117. For example, the wireless communication component 104 may communicate with the sensors 210 via the cable 117. The communication may be bidirectional including transfer of control signals for operating the intraluminal device 102 and sensor measurements collected by the sensors 210. In addition, the wireless communication component 104 and the sensors 210 may receive power from the power source 240 via the cable 117.

The wireless communication component 104 includes a transceiver (Tx/Rx) 252 and an antenna 254. The transceiver 252 may include hardware and/or software configured to perform data framing, data encoding/decoding, scrambling/descrambling, modulation/demodulation, and/or error encoding/decoding, for example, according to a pre-determined wireless communication protocol, such as Bluetooth, Zigbee, or UWB. In some embodiments, the transceiver 252 may include analog-to-digital converters (ADCs) and digital-to-analog converters (DACs). The antenna 254 may be constructed from a metal thin film or a metal thin wire. The antenna 254 may have any suitable dimension and may vary depending on the wireless technology in use and the specific design. In some embodiments, the antenna 254 may have a length between about 30 millimeters (mm) to about 60 mm. The transceiver 252 and the antenna 254 may be arranged in various configurations within the intraluminal device 102, as described in greater detail herein.

Although not shown, the intraluminal device 102 may include other components and/or circuitries, such as voltage signal converters, ADCs, DACs, line drivers, amplifiers, encoder/decoder logics, for facilitating the operations of the intraluminal device 102.

In operation, the intraluminal device 102 is inserted into a vessel, such as the vessel 120, of a patient and the sensors 210 may be in fluid communication with environments of the vessel. The sensors 210 may directly measure pressure and/or velocity of the fluid in the vessel. In one embodiment, the wireless communication component 104 may receive sensor control signals from the wireless communication component 130. The wireless communication component 104 may transfer the sensor control signals to the sensors 210. The sensor control signals may activate or deactivate the sensors 210. Once the sensors 210 are activated, the sensors 210 may continuously report pressure measurements at a present operating frequency. In another embodiment, the sensors 210 may be activated once the sensors 210 once the power source 240 is activated to provide power to the sensors 210. The sensor output signals carrying the measurements are typically relatively weak (e.g., low power levels). Thus, the transceiver 252 may include additional circuitry for conditioning the sensor output signals prior to transmission to the sensor measurement processing system 132. Signal conditioning may include analog and/or digital processing. Signal conditioning may include filtering and/or amplification.

Figure 3:
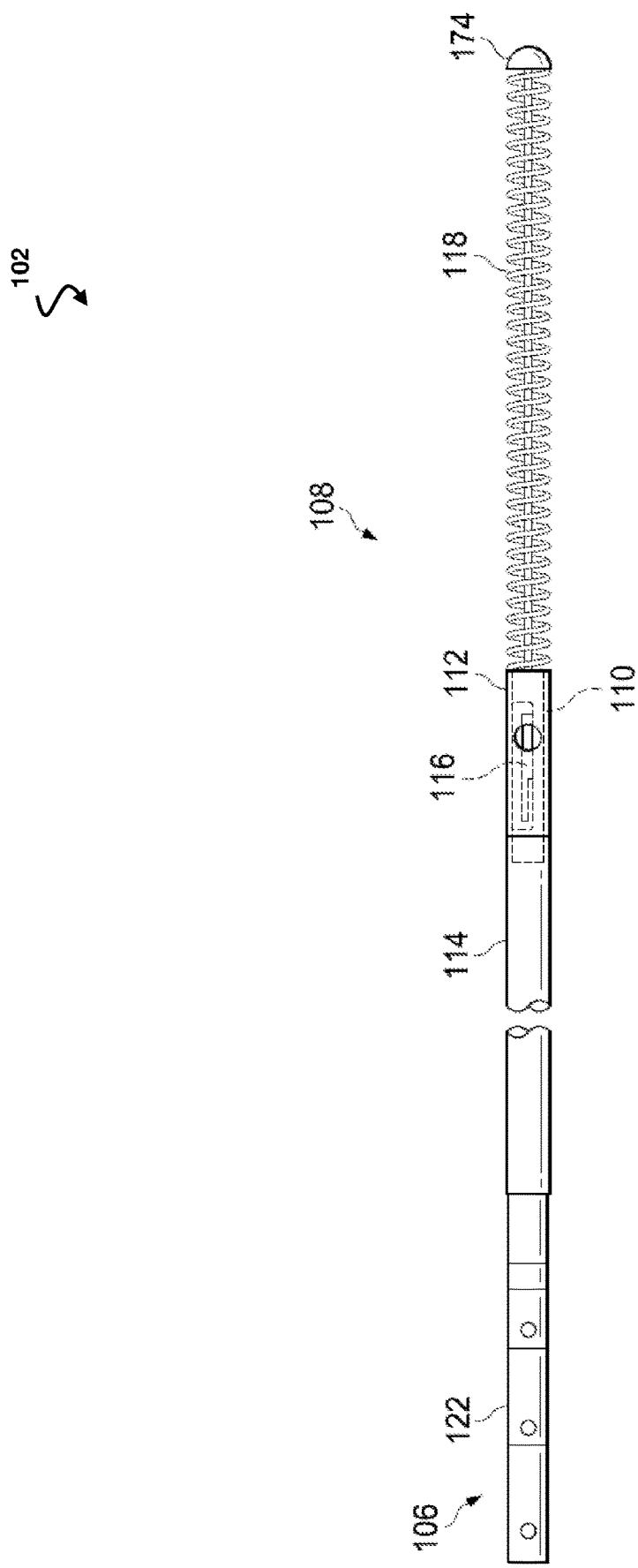
FIG. 3 is a perspective view of an intraluminal device, according to aspects of the present disclosure.
Figure 4:
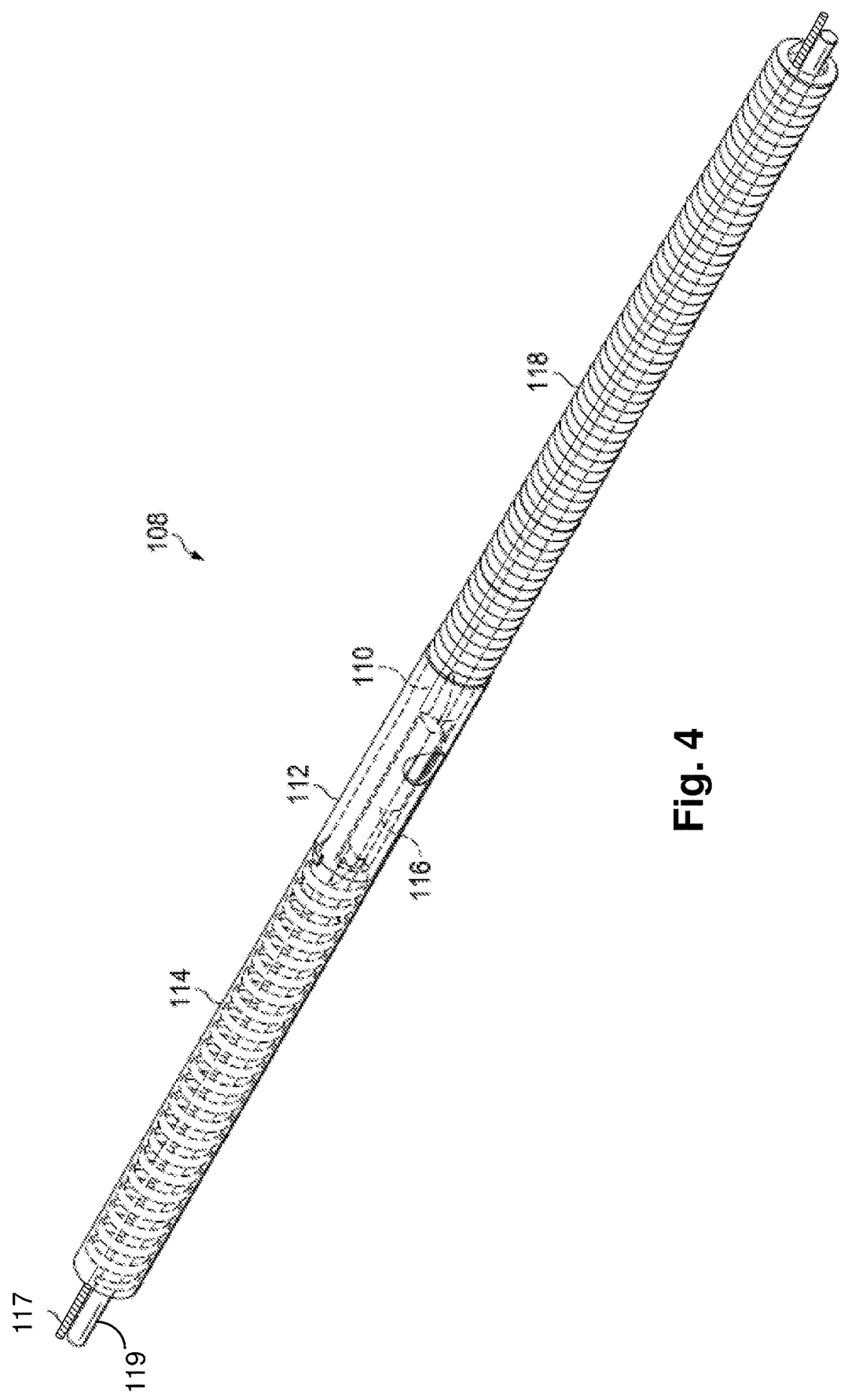
FIG. 4 is a perspective view of a portion of an intraluminal device, according to aspects of the present disclosure.

FIG. 3 is a perspective view of the intraluminal device 102, according to aspects of the present disclosure. FIG. 4 is a perspective view of a portion of the intraluminal device 102, according to aspects of the present disclosure. The intraluminal device 102 includes an internal sensor mount 110, the external housing 112, sensor assembly 116, a proximal flexible member 114, a distal flexible member 118, and a proximal electrical interface 122.

The proximal electrical interface 122 is configured to electrically connect the sensor assembly 116, the wireless communication component 104, and the power source 240 in order to communicate signals to the sensor measurement processing system 132. In accordance with this, the electrical interface 122 is in electrical communication with the sensor assembly 116. The electrical interface 122 may include a series of conductive contacts on its outer surface that engage and communicate with corresponding contacts on a connector, as described in greater detail herein.

The sensor assembly 116 may include one or more sensors 210. The sensor assembly 116 is arranged and configured to measure a physiological characteristic of a patient. When used on the intraluminal device 102, the sensor assembly 116 is arranged and configured to measure a physiological characteristic of a vessel itself, such as a vascular vessel. In one embodiment, the sensor assembly may include a pressure monitoring element configured to monitor a pressure within a lumen of the vessel 120. The pressure monitoring element can take the form of a piezo-resistive pressure sensor, a piezo-electric pressure sensor, a capacitive pressure sensor, an electromagnetic pressure sensor, an optical pressure sensor, and/or combinations thereof.

In some instances, one or more features of the pressure monitoring element are implemented as a solid-state component manufactured using semiconductor and/or other suitable manufacturing techniques.

In another embodiment, the sensor assembly may include a flow monitoring element configured to monitor a flow within a lumen of the vessel 120. The flow monitoring element may be a flow velocity sensor or a flow volume sensor. In another embodiment, the sensor assembly may include a temperature sensor configured to monitor the temperature within a lumen of the vessel 120.

In yet other embodiments, the sensor assembly 116 includes a plurality of sensors arranged to detect one or more characteristics of the patient and provide feedback or information relating to the detected physiological characteristic(s). The sensor assembly 116 may be disposed, for example, less than about 5 cm from a distal-most end 174 of the intraluminal device 102. In one embodiment, the sensor assembly 116 is disposed about 3 cm from the distal-most end 174 of the intraluminal device 102.

The intraluminal device 102 includes a cable 117 extending from the sensor assembly 116 to the proximal electrical interface 122. The cable 117 may include conductors, which may be electrical cables or wires configured to carry signals and/or power between the sensor assembly 116 and the proximal electrical interface 122. In some embodiments, the conductors are integrated with a core wire 119, which can extend along a length of the intraluminal device 102 with the core wire 119. In some embodiments, three conductors are provided; however, the number of conductors in any particular embodiment may depend in part on the type or number of sensors disposed within the intraluminal device 102. For example, the number of conductors can be in the range of about one to twenty conductors, one to ten conductors, one to five conductors, one to four conductors, one to three conductors, etc.

The external housing 112 is positioned between the proximal flexible member 114 and the distal flexible member 118, and is configured to cover and protect the sensor assembly 116. In an embodiment, the sensor assembly 116 may be mounted within the internal sensor mount 110, which may be a short tube or a hypotube, using epoxy.

The proximal flexible member 114 extends proximally from the internal sensor mount 110 towards the proximal electrical interface 122. The proximal flexible member 114 may be a polymer tube, a coil-embedded polymer tube, or a coil. The distal flexible member 118 may be similar to the proximal flexible member 114 and may include a radiopaque coil. The intraluminal device 102 further includes a distal-most end 174. The distal-most end 174 may be rounded end that can smoothly slide against tissue as the intraluminal device 102 is fed through the vasculature of a patient.

FIGS. 5-8 illustrate several configurations for placing or positioning the power source 240 and the wireless communication component 104 within the wireless intraluminal device 102. The power source 240 can be positioned in a connector 260 coupled to the proximal end of the intraluminal device 102. In an embodiment, the power source 240 may have an electrical storage capacity between about 5 milliampere hours (mAhr) and about 200 mAhr. In some embodiments, the power source 240 may include super capacitors with capacitances greater than 5 Farad (F). Dimensions of the power source 240 may vary depending on the capacity and structure of the connector 260 in which the power source 240 resides.

Since the maneuverability of the intraluminal device 102 is important, the connector 260 may be configured to be detachable. For example, a physician may maneuver the intraluminal device 102 (e.g., the flexible elongate member 158) into a location of interest within a patient body with the connector 260 detached. The physician may connect the connector 260 after the intraluminal device 102 is at the location of interest. For example, the electrical interface 122 of the intraluminal device 102 may be in electrical contacts with the power source 240 for transporting power when the intraluminal device 102 performs sensing measurements. In addition to allowing a physician to maneuver the intraluminal device 102 without the weight of the power source 240 and the connector 260, the detachable connector 260 allow for reuse of the connector 260 since intraluminal devices are typically single-use devices. The detachable connector 260 may be sterilized after each use.

The antenna 254 and the transceiver 252 of the wireless communication component 104 may be positioned in various locations within the intraluminal device 102 and/or the connector 260. In an embodiment, the antenna 254 and the transceiver 252 may be positioned within the connector 260. In such an embodiment, the transfer of sensor control and output signals between the sensor assembly 116 and the wireless communication component 104 crosses the electrical interface 122. The electrical interface 122 can introduce noise and degrades the signal integrity since the attaching and detaching of the connector 260 may introduce dirt (e.g., blood and saline fluid) to the electrical interface 122. Sensor output signals are typically low-power signals, and thus may be sensitive to noise. As such, at least the transceiver 252 may be placed within the flexible elongate member 158 to avoid transferring sensor output signals across the electrical interface 122. In some embodiments, the flexible elongate member 158 may have a diameter between about 0.010" and about 0.050", with some particular embodiments having a diameter of about 0.014", about 0.018", or about 0.035". The transceiver 252 may be an integrated chip (IC) with a form factor that fits into the flexible elongate member 158.

Figure 5:
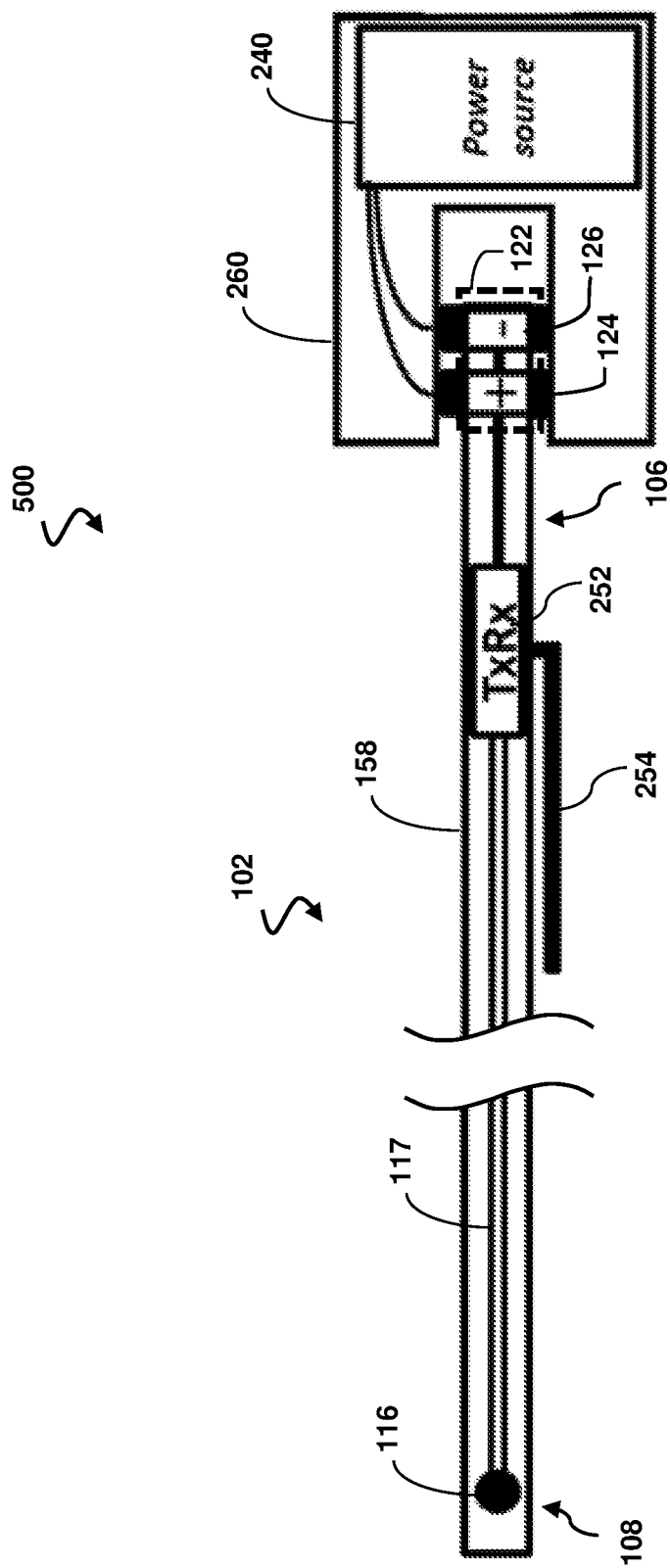
FIG. 5 is a schematic diagram illustrating a configuration of a wireless intraluminal device, according to aspects of the present disclosure.

FIG. 5 is a schematic diagram illustrating a configuration 500 of the wireless intraluminal device 102, according to aspects of the present disclosure. In the configuration 500, the sensor assembly 116 including the sensors 210 is positioned at the distal portion 108 of the flexible elongate member 158 near the distal end. The power source 240 is positioned within the detachable connector 260. The electrical interface 122 is configured to couple the cable 117 to the power source 240. The electrical interface 122 includes electrical contacts 124 and 126. For example, the electrical contacts 124 and 126 are coupled to a positive terminal (e.g., at a source voltage level) and a negative terminal (e.g., ground voltage level) of the power source 240, respectively, via electrical contacts of the connector 260. In the configuration 500, the transceiver 252 is positioned within the proximal portion 106 of the flexible elongate member 158 and adjacent and distal to the electrical interface 122. For example, the transceiver 252 may be positioned at a distance of about 1 cm to about 30 cm from the proximal-most end of the intraluminal device 102. In some particular embodiments, the transceiver 252 may be positioned at a distance of about 1 cm to about 3 cm from the proximal-most end of the intraluminal device 102. The transceiver 252 may be electrically coupled to the cable 117.

The antenna 254 extends from the wireless transceiver 252 and along an outer surface of the flexible elongate member 158. For example, the antenna 254 may extend along the outer surface such that a surface or a portion of the antenna 254 is exposed to ambient. Alternatively, the antenna 254 may be positioned close to the exterior surface of the flexible elongate member 158, but sealed by a coating or polymer layer such that the antenna 254 is not exposed to the ambient. The antenna 254 may extend towards the distal end and/or the proximal end. The antenna 254 may be configured in a flat position or coiled around the flexible elongate member 158. The transceiver 252 and the sensor assembly 116 may receive power from the power source 240 via the cable 117. As can be seen, the transceiver 252 may communicate with the sensor assembly 116 without crossing the electrical interface 122. Thus, the configuration 500 can provide robust transmission of sensitive, low-power sensor output signals.

Figure 6:
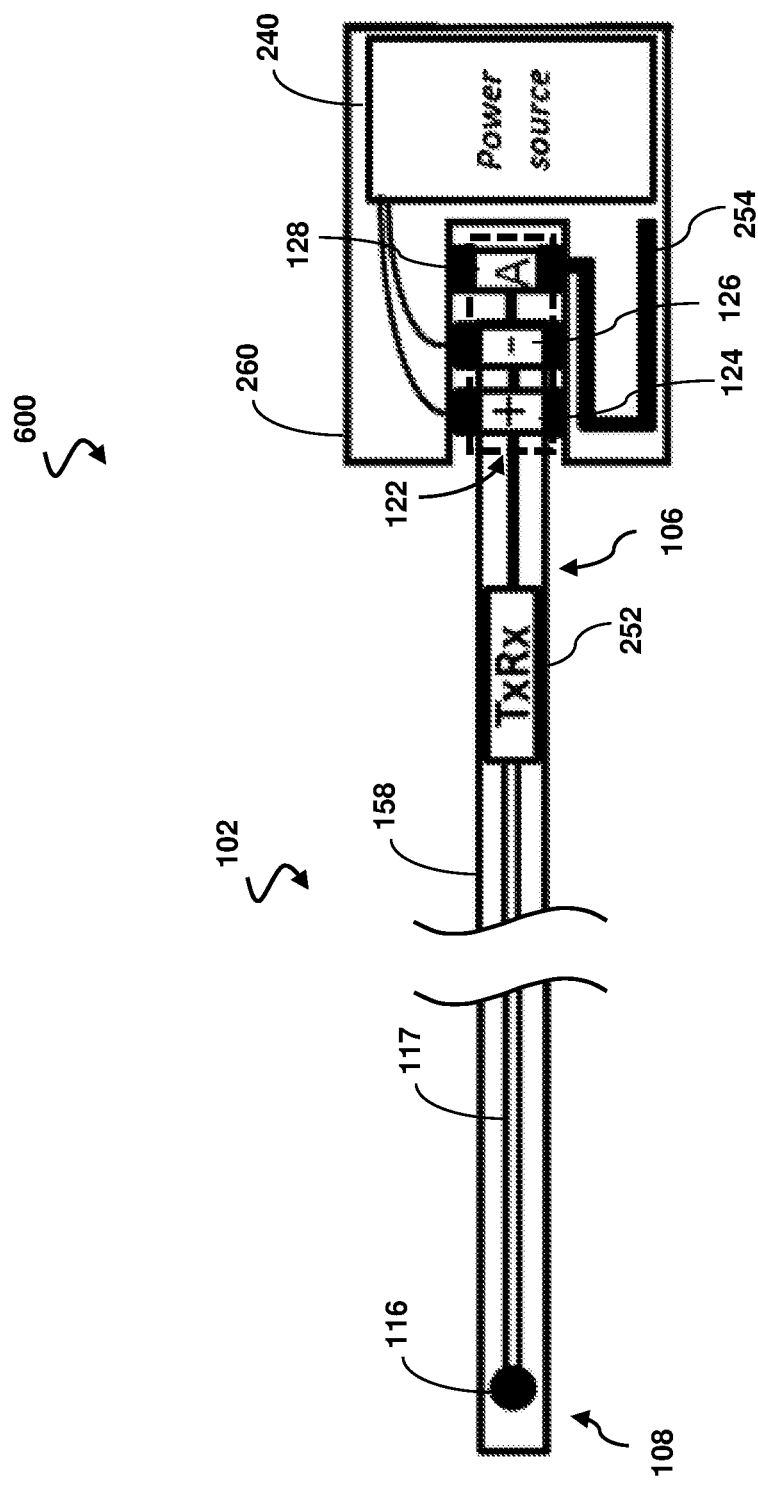
FIG. 6 is a schematic diagram illustrating a configuration of a wireless intraluminal device, according to aspects of the present disclosure.

FIG. 6 is a schematic diagram illustrating a configuration 600 of the wireless intraluminal device 102, according to aspects of the present disclosure. Similar to the configuration 500, the sensor assembly 116 is positioned near the distal end of the flexible elongate member 158 and the transceiver 252 is positioned within the flexible elongate member 158 and adjacent and distal to the electrical interface 122. However, the antenna 254 is positioned within the connector 260 instead of within the flexible elongate member 158 or on the surface of the flexible elongate member 158. To couple the antenna 254 to the transceiver 252 in the flexible elongate member 158, the electrical interface 122 further includes an electrical contact 128 coupled to the antenna 254 and the transceiver 252. Thus, the antenna 254 may communicate with the transceiver 252 via the cable 117. Although the communication between the antenna 254 and the transceiver 252 crosses the electrical interface 122, the transceiver 252 can receive weak sensor output signals from the sensor assembly 116 without crossing the electrical interface 122. The signals between the antenna 254 and the transceiver 252 typically have a higher power than the sensor output signals. Thus, positioning the antenna 254 within the connector 260 may have little impact to the transmission performance. The configuration 600 may benefit intraluminal devices with a limited space at the proximal end.

Figure 7:
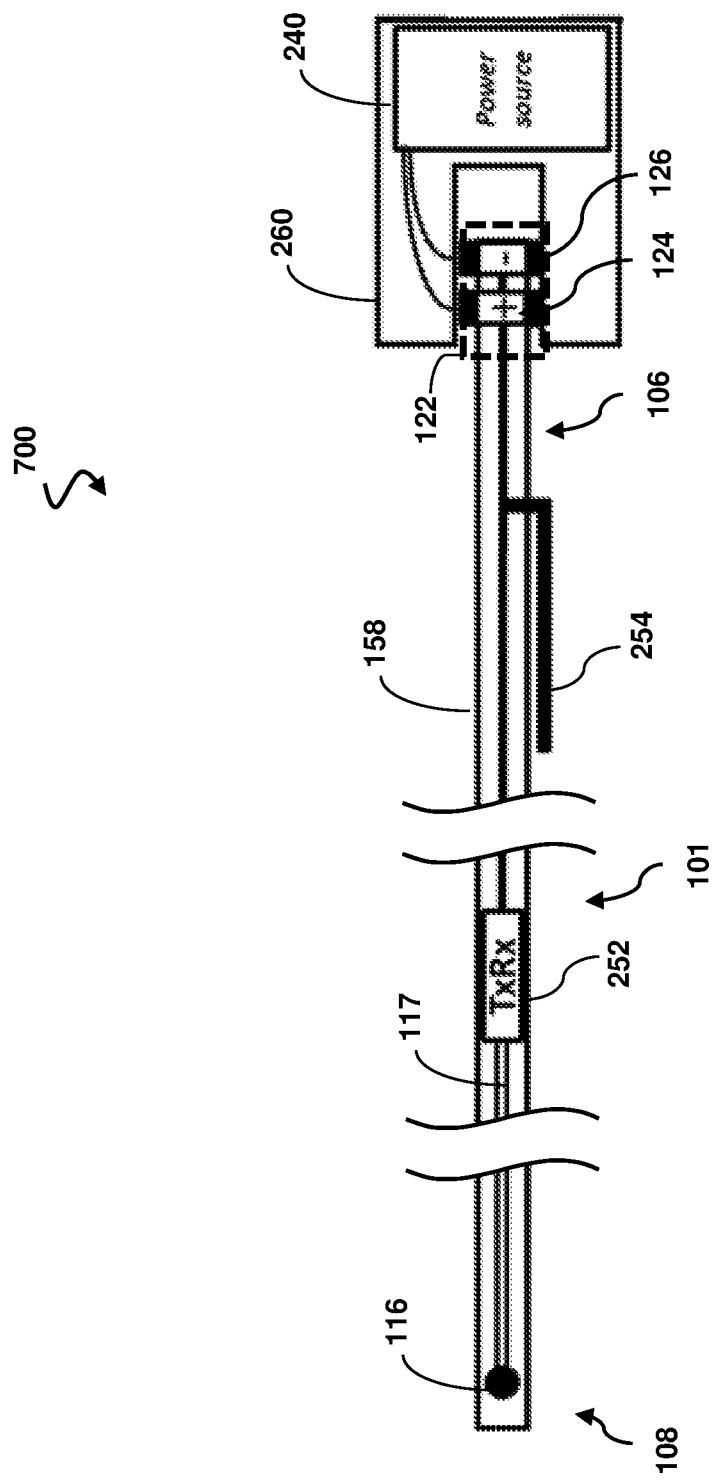
FIG. 7 is a schematic diagram illustrating a configuration of a wireless intraluminal device, according to aspects of the present disclosure.

FIG. 7 is a schematic diagram illustrating a configuration 700 of the wireless intraluminal device 102, according to aspects of the present disclosure. Similar to the configuration 500, the sensor assembly 116 is positioned near the distal end of the flexible elongate member 158 and the transceiver 252 is positioned within the flexible elongate member 158. However, the transceiver 252 is positioned at a central portion 101 of the flexible elongate member 158 instead of near the proximal end of the flexible elongate member 158. For example, the central portion 101 may be at least 30 cm from both the proximal-most end and the distal-most end of the intraluminal device 102. In some particular embodiments, the transceiver 252 may be positioned at a distance of about 25 cm to about 45 cm from the distal-most end of the intraluminal device 102. The antenna 254 is positioned at the same location (e.g., at the proximal portion 106) as in the configuration 500 so that the antenna 254 may remain outside of a patient body when the intraluminal device 102 is in use. As shown, the antenna 254 is positioned adjacent and distal to the electrical interface 122 and coupled to the cable 117. The antenna 254 extends from the cable 117 and along an outer surface of the flexible elongate member 158. The interconnect (e.g., the cable 117) in the intraluminal device 102 between the sensor assembly 116 and the transceiver 252 may contribute to signal degradation or signal loss. Thus, by positioning the transceiver 252 closer to the sensor assembly 116, the weak sensor output signals of the sensor assembly 116 may be transferred over a shorter distance on the cable 117 to reach the transceiver 252. Therefore, the configuration 700 may improve transmission performance when compared to the configuration 500. It should be noted that the antenna 254 may be positioned within the connector 260 as in the configuration 600, for example, when the space at the proximal end is limited, but the transmission performance may be compromised.

Figure 8:
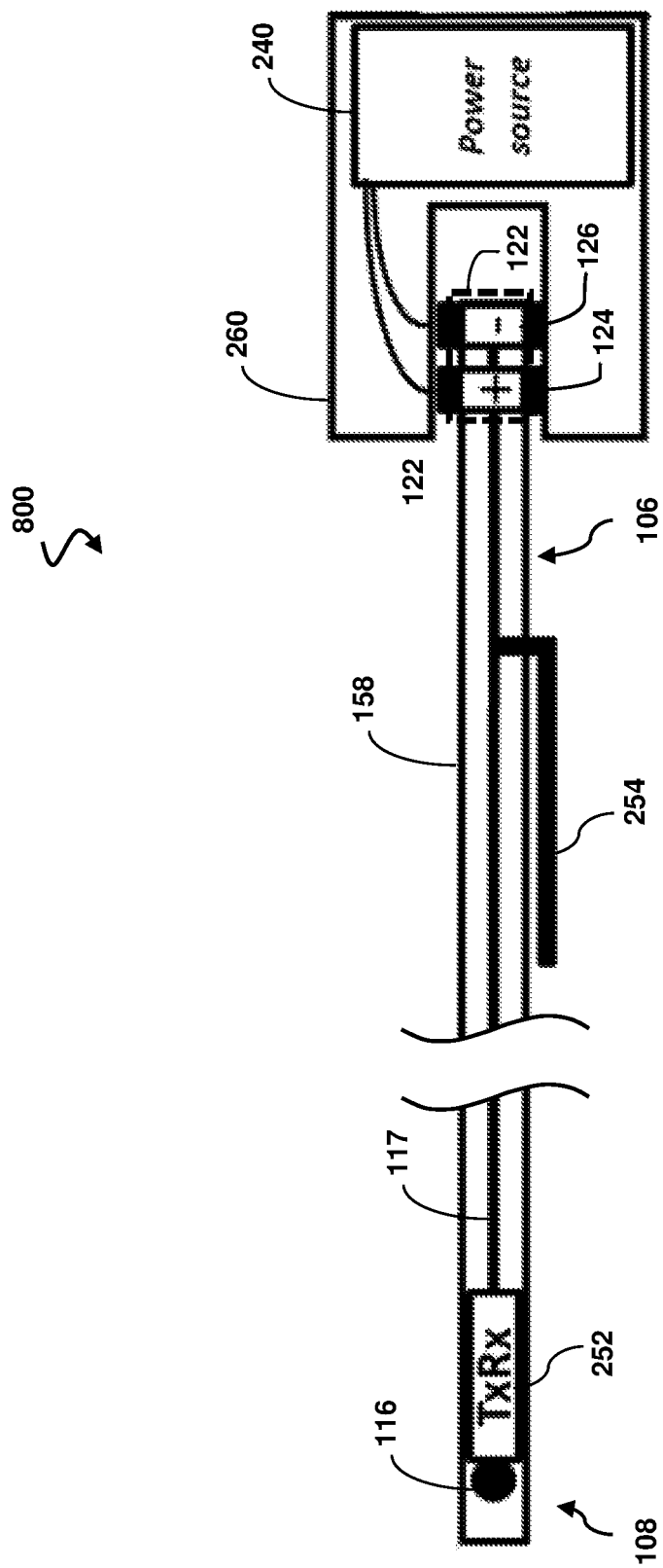
FIG. 8 is a schematic diagram illustrating a configuration of a wireless intraluminal device, according to aspects of the present disclosure.

FIG. 8 is a schematic diagram illustrating a configuration 800 of the wireless intraluminal device 102, according to aspects of the present disclosure. The configuration 800 is similar to the configuration 700, but the transceiver 252 is positioned at the distal portion 108 of the flexible elongate member 158 instead of at the central portion 101. As shown, the transceiver 252 is positioned adjacent to the sensor assembly 116. Thus, the distance between the sensor assembly 116 and the transceiver 252 is further reduced from the configuration 700. Therefore, the configuration 800 may provide further performance improvement when compared to the configuration 700.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:
1. A wireless intraluminal device, comprising:
a flexible elongate member including a proximal portion and a distal portion;
a sensor assembly coupled to the distal portion of the flexible elongate member;
a cable coupled to the sensor assembly and extending along the flexible elongate member;
a wireless transceiver positioned within the flexible elongate member, wherein the wireless transceiver is in communication with the sensor assembly via the cable;
an electrical interface coupled to the proximal portion of the flexible elongate member, wherein the electrical interface comprises a first electrical contact on an outer surface of the proximal portion and at least one second electrical contact on the outer surface of the proximal portion, wherein the first electrical contact is coupled to the wireless transceiver;
a connector comprising a power source and an antenna, wherein the proximal portion of the flexible elongate member is received within the connector,
wherein the first electrical contact is configured to provide communication between the antenna and the wireless transceiver such that the first electrical contact is positioned between the antenna and the wireless transceiver,
wherein the power source is coupled to the at least one second electrical contact of the electrical interface,
wherein the power source is configured to power the sensor assembly and the wireless transceiver, and
wherein the connector is detachable from the flexible elongate member.

2. The wireless intraluminal device of claim 1, wherein the wireless transceiver is positioned within the proximal portion of the flexible elongate member.

3. The wireless intraluminal device of claim 1, wherein the wireless transceiver is positioned within a central portion of the flexible elongate member between the proximal portion and the distal portion.

4. The wireless intraluminal device of claim 1, wherein the wireless transceiver is positioned within the distal portion of the flexible elongate member.

5. The wireless intraluminal device of claim 1, wherein the at least one second electrical contact includes two electrical contacts, wherein one of the two electrical contacts is coupled to a positive terminal of the power source and the other of the two electrical contacts is coupled to a negative terminal of the power source.

6. The wireless intraluminal device of claim 1, wherein the sensor assembly includes at least one of a pressure sensor or a flow sensor.

7. The wireless intraluminal device of claim 1,
   wherein the power source is positioned in the connector, and
   wherein the connector is coupled only to the proximal portion of the flexible elongate member.

8. The wireless intraluminal device of claim 1, wherein the antenna is positioned within the connector.

\* \* \* \* \*